US010213545B2

(12) United States Patent
Teranuma et al.

(10) Patent No.: US 10,213,545 B2
(45) Date of Patent: Feb. 26, 2019

(54) BODY-WALL-CONTACT-TYPE WATER TANK AND IN-CAVITY FLUID PERFUSION SYSTEM

(71) Applicant: NIKKISO CO., LTD., Tokyo (JP)

(72) Inventors: Masayuki Teranuma, Chiba (JP); Tatsuo Igarashi, Chiba (JP); Masashi Sekine, Chiba (JP); Yukio Naya, Ichihara (JP); Rongfu Lu, Higashimurayama (JP); Masanori Niiyama, Higashimurayama (JP); Yoshihiko Kinoshita, Tokyo (JP); Takuji Asano, Tokyo (JP); Manami Koshizuka, Tokyo (JP)

(73) Assignee: NIKKISO COMPANY, LTD., Tokyo (JP)

( * ) Notice: Subject to any disclaimer, the term of this patent is extended or adjusted under 35 U.S.C. 154(b) by 0 days.

(21) Appl. No.: 14/427,827

(22) PCT Filed: Sep. 20, 2013

(86) PCT No.: PCT/JP2013/075539
§ 371 (c)(1),
(2) Date: Mar. 12, 2015

(87) PCT Pub. No.: WO2014/046249
PCT Pub. Date: Mar. 27, 2014

(65) Prior Publication Data
US 2015/0238682 A1   Aug. 27, 2015

(30) Foreign Application Priority Data

Sep. 21, 2012 (JP) ................................. 2012-208089

(51) Int. Cl.
*A61B 1/32* (2006.01)
*A61M 3/02* (2006.01)
(Continued)

(52) U.S. Cl.
CPC ....... *A61M 3/0245* (2013.01); *A61B 17/0218* (2013.01); *A61B 17/3423* (2013.01);
(Continued)

(58) Field of Classification Search
CPC .......................... A61B 17/02–17/0293; A61B 17/3421–17/3439; A61M 3/0229–3/0262
See application file for complete search history.

(56) References Cited

U.S. PATENT DOCUMENTS 4,998,538 A * 3/1991 Charowsky ............ A61B 46/10
128/856
5,246,422 A   9/1993 Favre
(Continued)

FOREIGN PATENT DOCUMENTS

JP   H10-192297 A   7/1998
JP     3301614 B2   7/2002
(Continued)

OTHER PUBLICATIONS

Oct. 29, 2013 International Search Report issued in International Application No. PCT/JP2013/075539.
(Continued)

*Primary Examiner* — Nicholas J Plionis
*Assistant Examiner* — Steven J Cotroneo
(74) *Attorney, Agent, or Firm* — Oliff PLC

(57) ABSTRACT

A body-wall-contact-type water tank (12) is equipped with: a water-tank body for storing a fluid to be supplied into a body cavity, and positioned so as to contact a body wall (120); a through-hole which conveys the fluid stored in the water-tank body into the body cavity via an incision formed in the body wall (120), and which is formed in the bottom section of the water-tank body; and a connecting means for
(Continued)

connecting, in a fluid-tight manner, the water-tank body to the body wall (120) and/or to a retractor (110) attached to the incision.

9 Claims, 6 Drawing Sheets

(51) Int. Cl.

| | | |
|---|---|---|
| *A61B 17/02* | (2006.01) | |
| *A61B 17/34* | (2006.01) | |
| *A61M 13/00* | (2006.01) | |
| *A61M 1/00* | (2006.01) | |
| *A61B 90/00* | (2016.01) | |

(52) U.S. Cl.
CPC ....... *A61B 17/3474* (2013.01); *A61M 1/0058* (2013.01); *A61M 13/00* (2013.01); *A61B 2090/378* (2016.02)

(56) References Cited

U.S. PATENT DOCUMENTS

| | | | | |
|---|---|---|---|---|
| 5,328,478 A * | 7/1994 | McVay | ............... | A61M 1/0062 128/DIG. 12 |
| 5,336,171 A * | 8/1994 | Sugarbaker | ......... | A61M 3/0229 604/23 |
| 5,741,298 A * | 4/1998 | MacLeod | ............... | A61B 42/10 604/174 |
| 5,853,395 A * | 12/1998 | Crook | ............... | A61B 17/3423 600/208 |
| 5,906,577 A * | 5/1999 | Beane | ............... | A61B 17/0293 600/206 |
| 5,976,146 A | 11/1999 | Ogawa et al. | | |
| 6,371,968 B1 | 4/2002 | Kogasaka et al. | | |
| 6,382,211 B1 * | 5/2002 | Crook | ............... | A61B 17/0293 128/849 |
| 6,485,467 B1 * | 11/2002 | Crook | ............... | A61B 17/3423 604/174 |
| 7,473,221 B2 * | 1/2009 | Ewers | ............... | A61B 17/0293 600/208 |
| 7,951,076 B2 * | 5/2011 | Hart | ................... | A61B 17/0293 600/206 |
| 8,273,017 B1 * | 9/2012 | Moreno | ................... | A61B 1/32 600/203 |
| 8,485,970 B2 * | 7/2013 | Widenhouse | ...... | A61B 17/3462 600/201 |
| 9,198,647 B2 * | 12/2015 | Kleyman | ........... | A61B 17/3417 |
| 2008/0262527 A1 * | 10/2008 | Eder | ................... | A61B 17/3403 606/185 |
| 2009/0069759 A1 * | 3/2009 | Blott | ................... | A61M 1/0058 604/290 |
| 2010/0228094 A1 * | 9/2010 | Ortiz | ................... | A61B 17/3423 600/205 |
| 2010/0312061 A1 * | 12/2010 | Hess | ....................... | A61B 1/32 600/201 |
| 2011/0077587 A1 * | 3/2011 | Flom | ................... | A61M 3/0258 604/30 |

FOREIGN PATENT DOCUMENTS

| | | |
|---|---|---|
| JP | 2007-196023 A | 8/2007 |
| JP | 2012-081191 A | 4/2012 |
| WO | 98/35614 A1 | 8/1998 |

OTHER PUBLICATIONS

May 30, 2016 Search Report issued in European Patent Application No. 13838326.0.

Mar. 8, 2017 Office Action issued in Chinese Application No. 201380049251.2.

Apr. 21, 2017 Office Action issued in European Application No. 13 838 326.0.

\* cited by examiner

BODY-WALL-CONTACT-TYPE WATER TANK AND IN-CAVITY FLUID PERFUSION SYSTEM

TECHNICAL FIELD

The present invention relates to an in-cavity fluid perfusion system for perfusing a body cavity with a fluid such as an isotonic solution during a surgical operation, and a body-wall-contact-type water tank used for the in-cavity fluid perfusion system.

BACKGROUND ART

Existing laparotomy surgery, endoscopic surgery, and robot-assisted surgery are all categorized as surgical techniques performed in a condition where an internal organ is exposed to gas and gravity. In such a conventional surgical technique, the internal organ should be treated against gravity, which in turn requires that instruments, such as a forceps, for treating the organ have a certain degree of strength. As a result of this, the extent to which the diameter of the forceps may be minimized is limited. Further, when an ultrasonic diagnosis is conducted during a surgical operation, position of an ultrasound probe is restricted to specific locations.

Under the circumstances, it has been suggested that surgical operations be performed while a body cavity is perfused with a fluid such as an isotonic solution. For example, Patent Literature 1 discloses an apparatus for performing continuous perfusion and discharge of a physiological fluid for perfusion into and out of a body tissue or cavity of a human or an animal. On the other hand, Patent Literature 2 discloses a trocar suitable for perfusing a body cavity with a fluid. The trocar has an inner tube that constitutes a path for an endoscope and an outer tube that is concentrically arranged so as to cover an outer periphery of the inner tube. An end surface of the outer tube is provided with a fluid outlet for discharging the fluid and a fluid inlet for drawing the fluid.

PRIOR ART LITERATURE

Patent Literature

Patent Literature 1: Japan Patent No. 3301614
Patent Literature 2: JP 2012-081191 A

SUMMARY OF THE INVENTION

Problems Addressed by the Invention

However, in the techniques disclosed in Patent Literatures 1 and 2, the fluid is directly supplied from an opening having a relatively small diameter into the body cavity. To supply a large volume of fluid from the opening of the small diameter, a flow rate of the fluid is inevitably increased, with a result that a flow of the fluid tends to become turbulent. When the fluid discharged as such a turbulent flow is directly supplied into the body cavity, stream energy of the supplied fluid intensely disturbs the stored fluid within the body cavity. In this case, when there is a slightest amount of bleeding, blood drained into the fluid is rapidly diffused throughout the entire fluid within the body cavity, turning the entire fluid cloudy. Thus, there has been a problem of lowered visibility.

In view of the aforesaid current problem, the present invention aims to provide an in-cavity fluid perfusion system capable of perfusing a body cavity with a fluid such as an isotonic solution while preventing the fluid from being agitated inside the body cavity, and also provide a body-wall-contact-type water tank used in the system.

Means for Solving the Problems

The body-wall-contact-type water tank of the present invention includes a water tank main part placed in contact with a body wall and configured to retain a fluid that is fed into a body cavity, a through hole formed on a bottom section of the water tank main part for allowing the fluid stored in the water tank main part to flow into the body cavity via an incision that is made in the body wall, and a connecting means that connects the water tank main part, in a fluid-tight manner, to at least one of the body wall and a retractor fitted to the incision.

In a preferable aspect, the connecting means includes a connection mechanism for fluid-tightly connecting the bottom section of the water tank main part to the retractor. In another preferable aspect, the connecting means includes an attachment surface attached to the bottom section of the water tank main part and fluid-tightly bonded to the body wall.

In still another preferable aspect, a fluid feed nozzle for discharging the fluid into the water tank main part, or a mounting mechanism to which the fluid feed nozzle is detachably attached, is fixedly provided to the water tank main part. In this case, the fluid feed nozzle or mounting mechanism fixedly provided to the water tank main part is preferably arranged at such a position and attitude that allows the fluid discharged from the fluid feed nozzle to flow in an obliquely downward direction along an internal surface of the water tank main part. In a further preferable aspect, the water tank main part is composed of a material that is highly transmissive to ultrasonic waves.

An in-cavity fluid perfusion system according to another aspect of the present invention includes a body-wall-contact-type water tank including a water tank main part configured to store the fluid and placed in contact with the body wall and a through hole formed on a bottom section of the water tank main part for directing the fluid stored in the water tank main part into a body cavity via an incision that is made in the body wall, a feed means that feeds the fluid into the body-wall-contact-type water tank, a suction means that sucks, inside the body cavity, the fed fluid and discharges the fluid outside the body cavity, and a control means that controls actuation of the feed means and the suction means to perfuse the fluid.

Advantage of the Invention

According to the present invention, the fluid to be supplied into the body cavity is temporarily stored in the body-wall-contact-type water tank, which allows the fluid to flow into the body cavity stably and unidirectionally. As a result, agitation of the fluid within the body cavity can be effectively prevented.

EMBODIMENTS OF THE INVENTION

Figure 1:
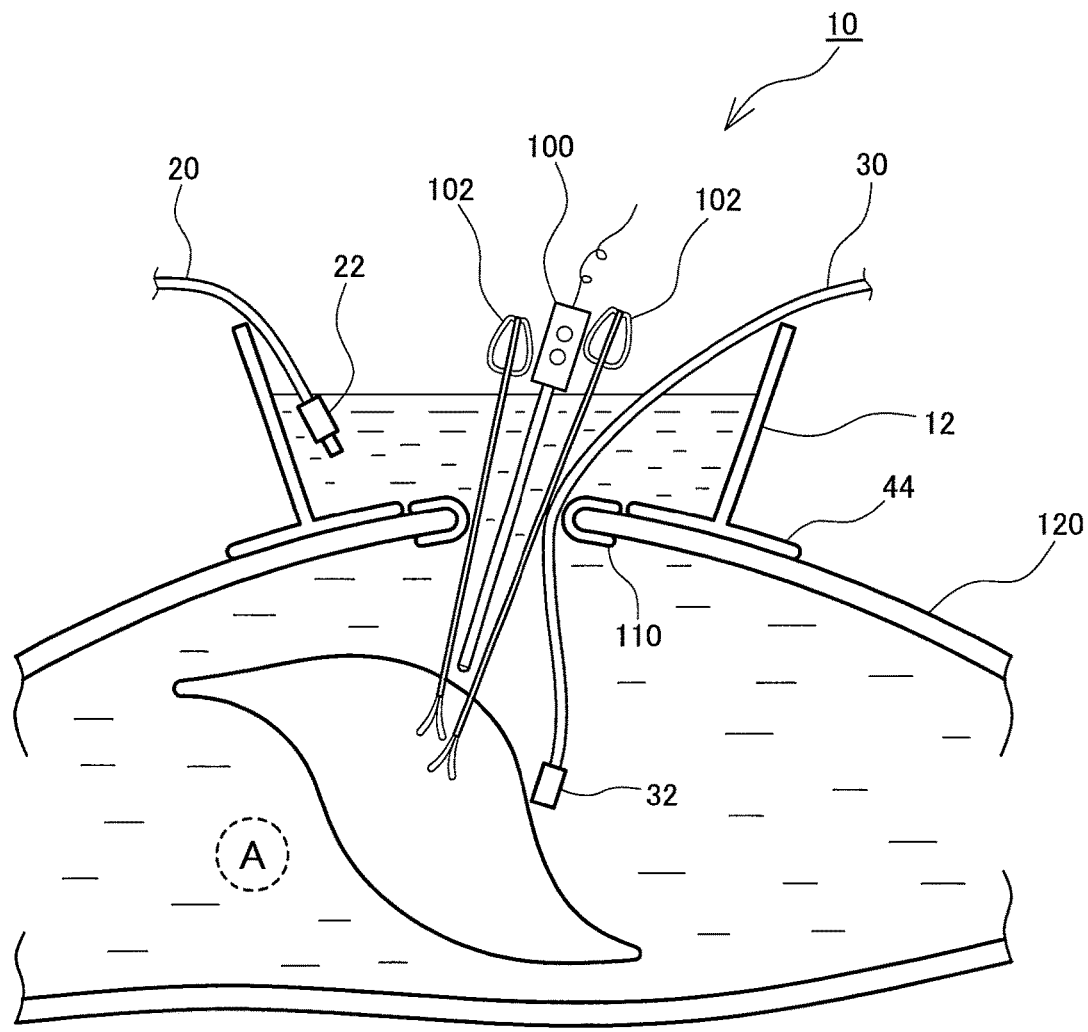
FIG. 1 is a schematic diagram showing an in-cavity fluid perfusion system according to an embodiment of the present invention.
Figure 2:
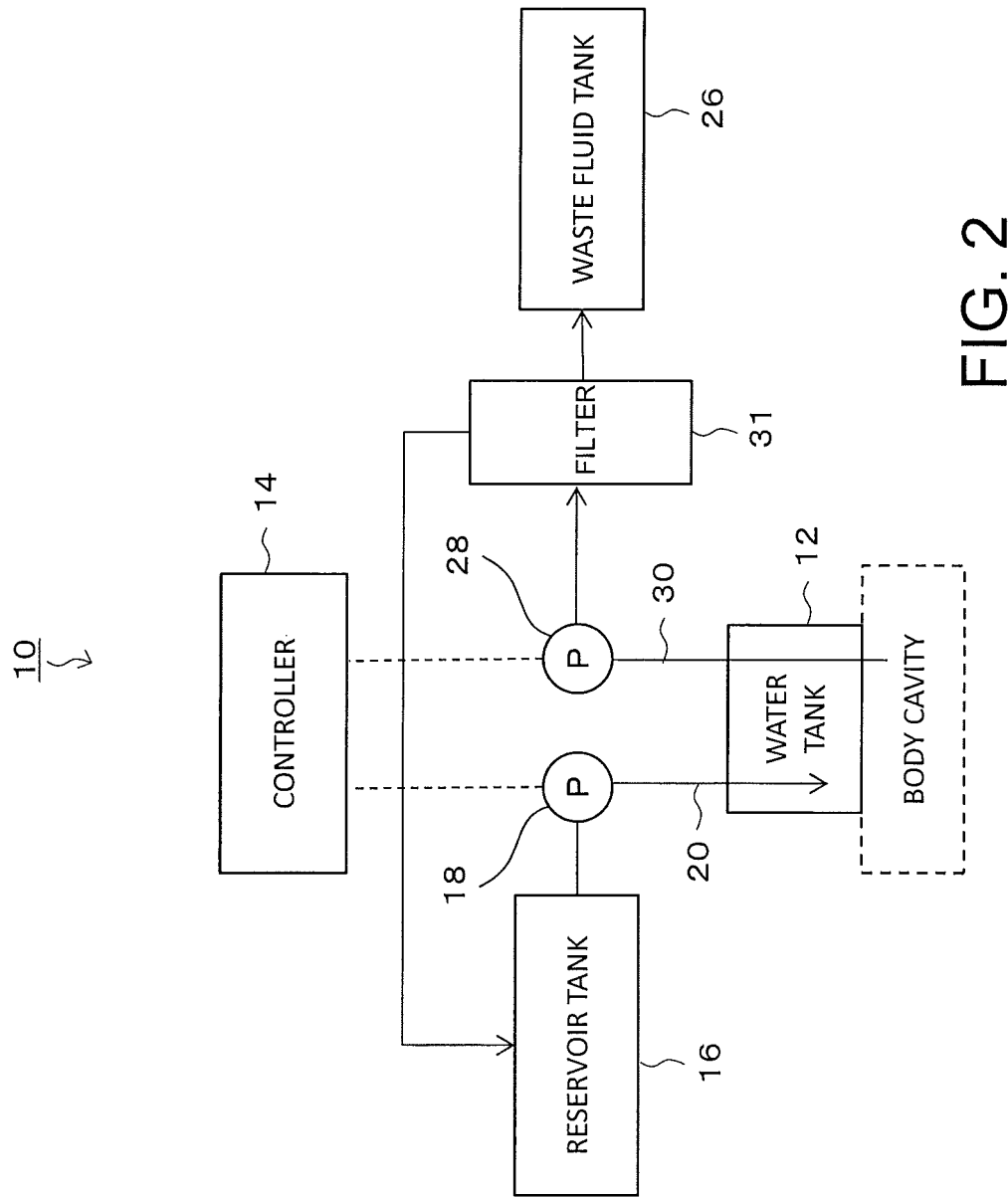
FIG. 2 is a block diagram showing components of the in-cavity fluid perfusion system.
Figure 3A:
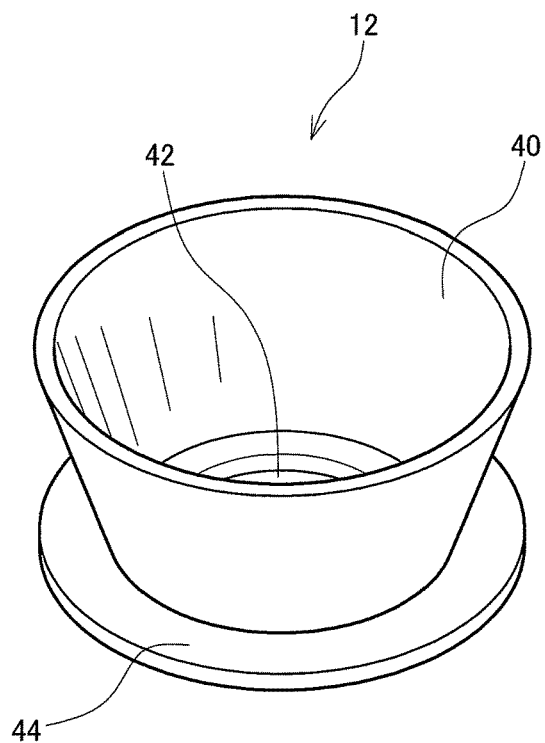
FIG. 3A is a perspective view of a water tank.
Figure 3B:
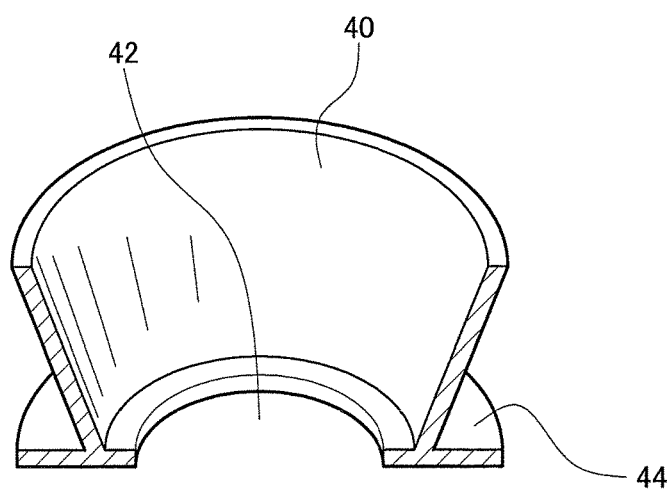
FIG. 3B is a cross sectional perspective view of the water tank.

In the following, embodiments of the present invention are described referring to the drawings. FIG. 1 is a schematic diagram showing the structure of an in-cavity fluid perfusion system 10 which is an embodiment of the present invention, and FIG. 2 is a block diagram of the in-cavity fluid perfusion system 10. Further, FIGS. 3A and 3B show a perspective view and a cross sectional view of a body-wall-contact-type water tank (hereinafter simply referred to as "water tank") 12.

To begin with, endoscopic surgery using the in-cavity fluid perfusion system 10 will be briefly explained. To perform the endoscopic surgery, an endoscope 100, a forceps 102, and other surgical instruments such as an electric cautery are inserted into a body cavity from a small incision that is made in a body wall 120 as shown in FIG. 1. Then, a surgical target site, such as an internal organ, is operated on or observed using the endoscope 100, the forceps 102 and other instruments. In this procedure, a retractor 110 is fitted to the incision for the purpose of stably opening the incision in a substantially circular shape and uniformly exerting a force on the incision. The retractor 110 is composed of a material which is of relatively high elasticity, such as silicone rubber. The retractor 110 is a substantially cylindrical component with flange sections outwardly extending from upper and lower ends of the retractor 110, respectively, and fitted into the incision by tucking the incision in between the flange sections formed on the upper and lower ends.

During a surgical operation, a fluid such as an isotonic solution is infused into the body cavity. A space sufficient for conducting the surgical operation can be secured by infusing the fluid as described above. Further, a buoyant force created by the infused fluid is exerted on the surgical target site such as an internal organ, which makes it possible to handle the surgical target site with a relatively small force. For this reason, an instrument which is of a small diameter and suitable for delicate processing may be used for the surgical instrument such as the forceps 102, in spite of the fact that such an instrument of small diameter is poor in rigidity. Still further, during the surgical operation, the need to conduct an ultrasonic diagnosis may arise in some cases. For a preferable ultrasonic diagnosis, it is necessary that air should be absent between an ultrasound probe and a target site to be observed. Accordingly, in conventional endoscopic surgery, positions of the ultrasound probe are often limited to specific locations where air can be avoided. On the other hand, when the body cavity is filled with the fluid, air existing around the target site to be observed is automatically excluded, which can lead to great improvement of flexibility in position of the ultrasound probe.

The in-cavity fluid perfusion system 10 is a system for perfusing the body cavity with the fluid in the thus-performed endoscopic surgery. The in-cavity fluid perfusion system 10 in this embodiment includes a water tank 12 placed in contact with a body wall 120, a feed mechanism that feeds the fluid into the water tank 12, a suction mechanism that sucks the fluid within the body cavity, and a controller 14 that controls actuation of the feed and suction mechanisms.

The feed mechanism is a mechanism for feeding the fluid such as the isotonic solution stored in a reservoir tank 16 through a feed pipe 20 into the water tank 12. An end of the feed pipe 20 is equipped with a fluid feed nozzle 22, and the fluid feed nozzle 22 is attached to the water tank 12. A feed pump 18 installed in the feed mechanism is driven and controlled by the controller 14. The suction mechanism is a mechanism for sucking the fluid retained in the body cavity, transporting the fluid through a suction pipe 30 to a filter 31, and subsequently separating the fluid such as the isotonic solution from waste components including blood and others in the filter 31. The fluid such as the isotonic solution obtained through the separation is sent to the reservoir tank 16 or the feed pipe 20, while the water components including blood and others are sent to a waste fluid tank 26. A suction port 32 attached to an end of the suction pipe 30 is inserted into the body cavity. A suction pump 28 installed in the suction mechanism is also driven and controlled by the controller 14. The controller controls actuation of the feed pump 18 and the suction pump 28 in accordance with an instruction from a user, to circulate the fluid through the body cavity.

The water tank 12 is a container seated on the body wall 120 and configured to retain the fluid. A main part 40 of the water tank 12 is formed in the shape of a roughly circular truncated cone whose diameter becomes greater on an upper side as shown in FIGS. 3A and 3B, and the top of the water tank 12 is completely open. On the bottom of the water tank 12, a circular through hole 42 is formed in a central area. The main part 40 seated on the body wall 120 communicates with an inside of the body cavity via the through hole 42 and the incision. Thus, the fluid retained in the main part 40 flows through the through hole 42 and the incision into the body cavity. The size of the through hole 42 is not specifically limited, but it is preferably greater than the incision. It should be noted that the size of the incision may be changed as appropriate depending on the nature of the surgical operation. When the operation is performed within a body cavity by means of an endoscope 100, the forceps 102, the electric cautery, and other instruments, for example, the incision may be relatively small and may be made so as to provide an opening of approximately 20 mm in diameter, for example. On the other hand, when the internal organ within the body cavity is drawn, by means of human hands, into the water tank 12 to perform the operation inside the water tank 12 (i.e. outside the body cavity), the incision is preferably made so as to provide an opening having a diameter large enough to accommodate human hands, for example, a diameter of approximately 70 mm, while the diameter of the through hole 42 is preferably also 70 mm or greater.

An outer circumferential edge of the bottom surface of the main part 40 has a substantially circular flange section which is outwardly projected therefrom. The flange section 44 may preferably have a suitable level of flexibility that allows the flange section 44 to follow a surface outline of the body wall 120.

The water tank 12 includes a connection mechanism for connecting the main part 40 to at least one of the body wall 120 and the retractor 110 in a fluid-tight manner. Various types of structure may be considered for the connection mechanism. For example, an adherent surface formed by applying a medical adhesive onto the bottom surface of the main part 40 may be used as the connection mechanism. In this case, the main part 40 and the body wall 120 are fluid-tightly connected to each other as shown in FIG. 1, by bringing the bottom surface (the adherent surface) of the main part 40 into close contact with the surface of the body wall 120 so as to adhere thereto.

Figure 4:
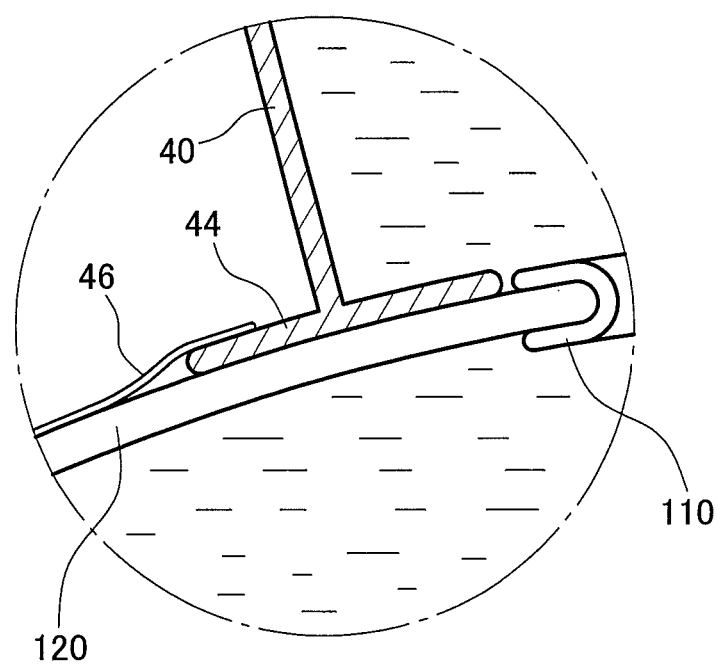
FIG. 4 is a diagram showing an example of a connection mechanism.

Further, alternatively or additionally, a surgical drape 46, which is attached via the flange section 44 to the main part 40 as shown in FIG. 4, may be used as a part of the connection mechanism. The surgical drape 46 is a waterproof sheet member that covers a region around a surgery site during an operation, and a medical adhesive having an excellent water resistant property is applied on one surface of the surgical drape 46. The surgical drape 46 is fixed to the entire circumference of the flange section 44 so as to outwardly extend therefrom. Then, when the water tank 12 is used, the surgical drape is brought into close contact with the surface of the body wall 120 and may be stuck thereon. Because, in the above-described structure, the main part 40 and the surface of the body wall 120 are connected to each other in the fluid-tight manner, it is possible to prevent the fluid that has escaped from the main part 40 leaking to the outside.

Figure 5:
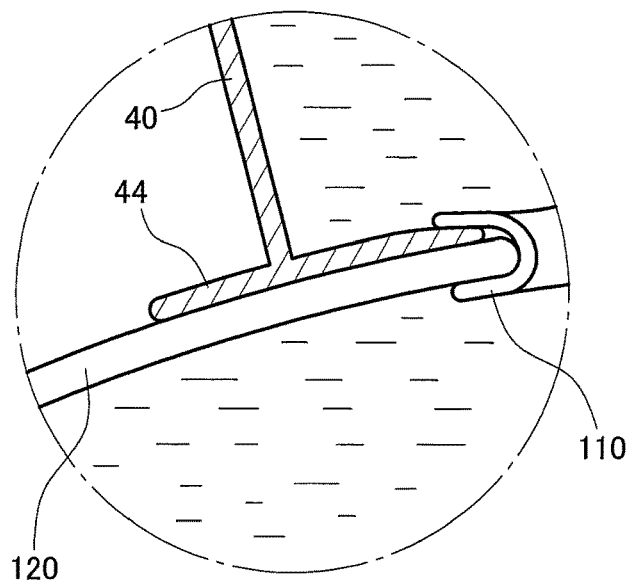
FIG. 5 is a diagram showing another example of the connection mechanism.
Figure 6:
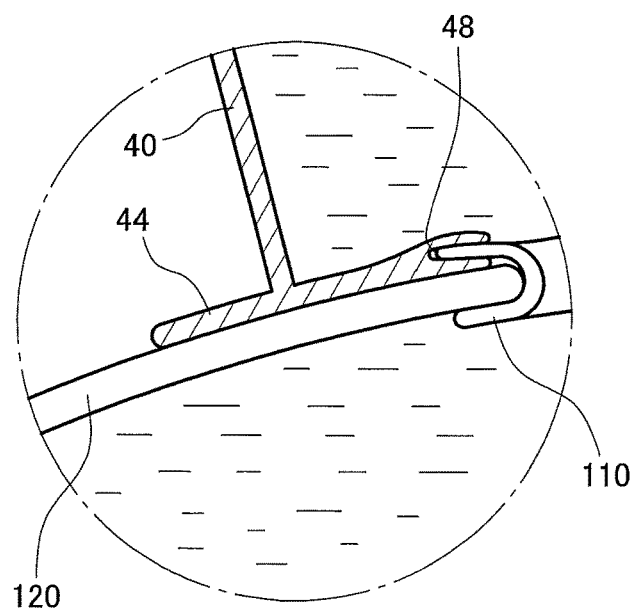
FIG. 6 is a diagram showing still another example of the connection mechanism.

Also, alternatively or additionally, an arrangement for fluid-tightly connecting the bottom surface of the main part 40 to the retractor 110 may be employed as a part of the connection mechanism. As shown in FIG. 5, for example, the inner diameter of the through hole 42 may be defined to be smaller than the outer diameter of the flange section of the retractor 110, and, in use, the bottom surface of the main part 40 may be slidingly inserted in between the flange section of the retractor 110 and the surface of the body wall 120. In this way, the arrangement for fluid-tightly connecting the main part 40 to the retractor 110 may be obtained. Moreover, as another embodiment, a groove 48 may be formed in an inner circumferential surface of the through hole 42 so as to hold therein a flange rim of the retractor 110, and in use, the flange rim of the retractor 110 may be inserted into the groove 48, to thereby obtain the arrangement for fluid-tightly connecting the main part 40 to the retractor 110. As still another embodiment, the main part 40 of the water tank 12 and the retractor 110 may be integrated into one piece. In other words, the water tank 12 itself may also function as the retractor 110.

On the other hand, rather than installing the connection mechanism in the water tank 12 itself, a component separate from the water tank 12 may be used to fluid-tightly couple the water tank 12 to the body wall 120 or the retractor 110. For example, leakage of the fluid may be prevented by bonding the flange section 44 to the body wall 120 by means of a surgical tape, which is a medical adhesive tape.

In the following, procedural steps of using the thus-structured in-cavity fluid perfusion system 10 will be described. The in-cavity fluid perfusion system 10 is used, as described above, when endoscopic surgery is performed. In use of the in-cavity fluid perfusion system 10, firstly, the water tank 12 is placed at a position where the through hole 42 of the water tank 12 is opposed to the incision, thereby causing the water tank 12 to communicate with the body cavity. Here, the main part 40 of the water tank 12 is connected to at least one of the body wall 120 and the retractor 110 in a fluid-tight condition such that the fluid within the water tank 12 does not leak to the outside.

After the main part 40 of the water tank 12 is properly set, the feed pump 18 is activated to feed the fluid into the water tank 12. The fluid fed into the water tank 12 subsequently flows from the water tank 12 through the through hole 42 and the incision into the body cavity. Then, after the body cavity becomes filled with the fluid, the fluid that is not allowed to enter the body cavity is accumulated in the water tank 12, raising a level of the fluid inside the water tank 12.

Subsequent to the fluid inside the water tank 12 reaching a predetermined level, the suction pump 28 is also activated to suck the fluid within the body cavity. Here, a suction flow rate is set to a value substantially equal to a feed flow rate. In this way, an approximately constant fluid level is maintained inside the water tank 12, while the body cavity is continuously supplied with new fluid. After this state is established, an operator may insert the surgical instruments, such as the endoscope 100 and forceps 102, through the through hole 42 and the incision into the body cavity to perform observation or operation on the surgical target site.

In this state, the fluid is retained within the water tank 12, and after that, it is fed through the through hole 42 and the incision into the body cavity. In other words, the fluid discharged from the fluid feed nozzle 22 is retained within the water tank 12 for a certain period of time before reaching the body cavity. In this retention period, air bubbles entrained in the fluid are removed. As a result, the fluid with less air bubbles is supplied to the body cavity, which can help prevent visibility from being lowered by the air bubbles and prevent deterioration in accuracy (poor transmittance of an echo) of the ultrasonic diagnosis due to the air bubbles.

In addition, the fluid immediately after being discharged from the fluid feed nozzle 22 into the water tank 12 forms a relatively fast and turbulent flow that has great stream energy for agitating the fluid. However, because the stream energy diminishes gradually while the fluid is retained within the water tank 12, a flow of the fluid that reaches the body cavity becomes a laminar flow (or a virtually laminar flow) having smaller stream energy for agitation. Then, the fluid supplied to the body cavity in the form of the laminar flow is drawn toward the suction port 32 by a suction force from the suction pump 28. That is, according to this embodiment, a constant flow of the fluid directed to the suction port 32 without agitation is created inside the body cavity. Then, the thus-created constant flow can serve a useful function of effectively preventing an increase in turbidity of the fluid and consequent lowered visibility in an operative field.

More specifically, during a surgical operation, blood may be caused to flow into the fluid due to bleeding in some cases. In such a case, greater stream energy for agitation causes the blood to be diffused throughout the body cavity in a short time, increasing the turbidity of the fluid. Such an increased turbidity of the fluid lowers the visibility in the operative field, resulting in significant deterioration of operative efficiency. On the other hand, when the constant flow directed to the suction port 32 is created in the body cavity as in the case of the present embodiment, the blood that has leaked into the fluid is drawn to the suction port 32 without undergoing agitation. In this way, the lowering of visibility due to the increased turbidity can be effectively prevented. Particularly, in a case where massive hemorrhage occurs, it is possible to keep visually identifying a hemorrhagic spot according to this embodiment, which can lead to improvement of safety in operation.

Next, each component structure desirable for achieving the above-described perfusion in a more efficient way will be described. Firstly, a configuration of the suction mechanism is described in detail. The suction port 32 provided to the suction mechanism is preferably placed to one side of the surgical target site opposite to the incision. To put it another way with reference to FIG. 1, the suction port 32 is preferably placed in the vicinity of a position A. This is because even when the bleeding occurs, blood is constantly directed to flow in a direction away from the surgical target site toward the opposite side of the incision, and the visibility in the operative field can be accordingly prevented in an efficient manner from becoming deteriorated. Furthermore, even though the surgical target site is situated directly below the incision, it is preferable that the suction port 32 be located in a deeper region of the body cavity because the placement of the suction port 32 in a deeper side allows the warmed fluid to reach the deeper region (the deepest end) of the body cavity.

Meanwhile, although FIGS. 1 and 2 show the single suction pipe 30 and the single suction pump 28, more than one suction pipe and suction pump may be installed. For example, in addition to the suction pipe 30 and the suction pump 28 used for treating a typically expected level of bleeding, an emergency suction pipe 30 and an emergency suction pump 28 that are activated only when massive hemorrhage occurs may be installed. In this case, a suction port 32 for the emergency suction pipe 30 is preferably provided in the vicinity of the surgical target site.

Figure 7:
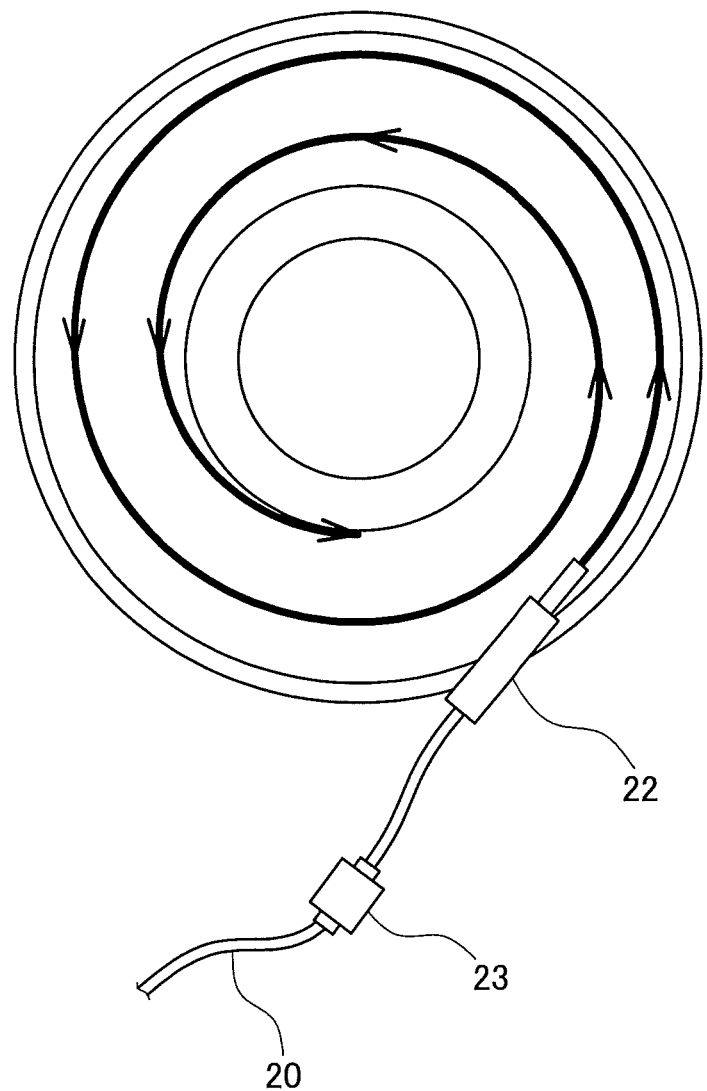
FIG. 7 is a diagram showing a mode of placing a fluid feed nozzle.

Besides, the fluid feed nozzle 22 attached to the feed mechanism is preferably arranged as shown in FIG. 7 with its tip end oriented in an obliquely downward direction, and placed so as to follow the inner surface of the main part 40 of the water tank 12. When the fluid is delivered along the inner surface of the main part 40 of the water tank 12 by arranging the fluid feed nozzle 22 as described above, a swirling flow, a so-called spiral flow, is created within the water tank 12. The spiral flow keeps the fluid, which is made cloudy by blood or the like, from flowing backward to a water tank 12 side from the body cavity. Here, to facilitate installation of the fluid feed nozzle 22 at the appropriate position and attitude, a fixture mechanism for the fluid feed nozzle 22 (a holder of the fluid feed nozzle 22) is preferably installed in the water tank 12, or the fluid feed nozzle 22 itself is fixed to the water tank 12. In a case where the fluid feed nozzle 22 is fixed to the water tank 12, it is also preferable that the fluid feed nozzle 22 is coupled to a connector 23 to which or from which an end of the feed pipe 20 can be easily attached or removed.

The feed and suction flow rates of the fluid during the operation are not specifically limited, and may be set to any rate at which a suitable view field can be maintained even when bleeding occurs. In addition, the feed and suction flow rates of the fluid are not necessarily maintained constant, and may be changed in accordance with the level of bleeding.

For example, while there is no bleeding, the feed and suction flow rates may be lowered, or feeding and/or suction may be completely stopped depending on the circumstances. On the other hand, when bleeding occurs, the feed and suction flow rates may be set to a relatively greater rate of from 1600 ml/min to 2500 ml/min, for example. The values of the feed and suction flow rates of the fluid may be determined by an operator in accordance with a visually checked level of turbidity of the fluid (the presence or absence of bleeding). In a further embodiment, a turbidity sensor may be installed to detect the level of turbidity of the fluid, and according to a detection value from the turbidity sensor, the controller 14 may automatically control the actuation of each pump (the values of feed and suction flow rates).

It should be noted that an increase in feed and/or suction flow rate can lead to a great change of the fluid level in the water tank 12. Such a great change consequently raises the possibility that the fluid will spill out from the water tank 12, or an internal organ inside the body cavity will be exposed to ambient air due to a shortage of the fluid. In this regard, ticks may be marked on a wall surface of the water tank 12 to indicate upper and lower limit values of the fluid level. Provision of the ticks allows a user to find at a glance whether or not the present level of the fluid is appropriate. Then, in a case where the fluid level is insufficient, the feed flow rate may be increased (or the suction flow rate may be decreased), while in a case where the fluid level is excessively high, the feed flow rate may be decreased (or the suction flow rate may be increased). Alternatively, a level gauge may be installed inside the water tank 12 in another embodiment, and the controller 14 may be configured to automatically adjust actuation of each pump depending on a detection value (the fluid level) detected by the level gauge.

Next, a desirable shape and size of the water tank 12 will be described. The main part 40 of the water tank 12, which is described as the substantially circular truncated cone in the above, may be modified to be a different shape, such as a rectangular parallelepiped, for example, as long as the through hole 42 can be formed at least on the bottom surface. However, in light of creation of the above-described spiral flow, it is preferable that the main part 40 has a substantially circular shape in cross section, and may be, for example, in the shape of the circular truncated cone or a cylinder.

Preferably, the size of the water tank 12 is defined depending on a type of surgical operation (an expected level of bleeding), the body shape of a patient, capabilities of the feed and suction pumps, and other factors. More specifically, the applicant found by experiment that, in light of quick recovery of the view field in the event of occurrence of bleeding, it is desirable that the feed and suction flow rates of the fluid lie in a range of from 1600 ml/min to 2500 ml/min (note that the values indicated here may, of course, vary greatly depending on the type of surgical operation and the expected level of bleeding). Further, for allowing the fluid fed in the water tank 12 to be sent as the laminar flow to the body cavity, the fluid should be retained within the water tank 12 for a certain length of time (such as 12 seconds, for example). When the retention time necessary for creating the laminar flow is taken as T (sec) and the feed/suction flow rate of the fluid is taken as V (ml/min), it is desired that the water tank 12 should retain at least an amount of $X=T*V/60$ (ml) of fluid. The volumetric capacity of the water tank 12 is preferably set to a size capable of safely retaining the amount X of fluid, i.e. a size large enough to keep the fluid from spilling out of the water tank 12 even when the water tank 12 is slightly inclined. Preferably, the volumetric capacity of the water tank 12 may be from approximately 1.3·X to approximately 1.6·X, for example.

To give a specific example, assuming that the feed and suction flow rates of the fluid are 2500 ml/min and the retention time necessary for creating the laminar flow is 12 sec, the amount X of the fluid to be retained in the water tank 12 is 500 ml. Then, the water tank 12 is preferably defined to be of the volumetric capacity of from approximately 650 to approximately 800 ml in order to safely store 500 ml of the fluid without spilling.

Further, a cross sectional area of the water tank 12 is preferably determined based on both the amount (volume) X of the fluid to be retained in the water tank 12 and a required fluid level in the water tank 12. The required fluid level in the water tank 12 may be determined based on workability inside the water tank 12, a magnitude of a load exerted on the internal organ, and the like. More specifically, the internal organ in the body cavity may be, in some cases, extracted from the body cavity into the water tank 12 and operated on within the water tank 12 depending on the nature of the operation. In this case, to prevention the internal organ from being exposed to ambient air, it is preferable that the fluid level in the water tank 12 be at least higher than the thickness of the extracted internal organ. On the other hand, a hydraulic pressure to be applied to a patient's organ within the body cavity is determined from the level of the fluid retained in the main part 40 of the water tank 12. In light of a reduced burden on the organ, it is preferable that the hydraulic pressure and therefore the fluid level be minimized as much as possible. Taking into account various conditions as described above, the required fluid level in the water tank 12 is defined as appropriate, and the cross sectional area of the water tank 12 is preferably determined based on the fluid level and the value of the amount X of the fluid to be stored.

Meanwhile, the material of the water tank 12, which is not specifically limited as long as the material can resist the hydraulic pressure, preferably has an appropriate degree of elasticity capable of undergoing geometrical changes following the surface of the body wall 120. In addition, it is more preferable that the water tank 12 be desirably formed of a material that does not hamper the ultrasonic diagnosis. To be more specific, the material that does not hamper the ultrasonic diagnosis is a material that is highly transmissive to ultrasonic waves and has an acoustic impedance close to that of liquid, such as silicon, for example. Moreover, although the water tank 12 preferably has sufficient strength to be selfstanding while storing the fluid, any supplementary member may be used to support the water tank 12. For example, when there is a difficulty in making the water tank 12 selfstanding, an upper end of the main part 40 of the water tank 12 may be held in a suspended state by means of an articulated arm mechanism or the like to prevent the water tank 12 from overturning.

It should be noted that although FIG. 1 is a diagram created on the assumption that the operation is performed on an abdominal cavity, the in-cavity fluid perfusion system of this embodiment may be applied to treatments of an eye or a joint, in the field of obstetrics and gynecology, and in the urological field. The shape and size of the water tank may be flexibly changed depending on characteristics of a surgical target site.

REFERENCE NUMERALS

10 in-cavity fluid perfusion system, 12 body-wall-contact-type water tank, 14 controller, 16 reservoir tank, 18 feed pump, 20 feed pipe, 22 fluid feed nozzle, 23 connector, 26 waste fluid tank, 28 suction pump, 30 suction pipe, 31 filter, 32 suction port, 40 main part, 42 through hole, 44 flange, 46 surgical drape, 48 groove, 100 endoscope, 102 forceps, 110 retractor, 120 body wall.

The invention claimed is:

1. A body-wall-contact-type water tank comprising:
   a water tank main part that includes a bottom-most surface, the bottom-most surface of the water tank main part being configured to be in contact with an outer surface of a patient's body wall for retaining a liquid that is fed into a body cavity of the patient;
   a through hole formed in the bottom-most surface of the water tank main part, the through hole being configured to direct the liquid retained in the water tank main part into the patient's body cavity via an incision that is made on the patient's body wall, and
   a flange section outwardly extended from an outer circumferential edge of the bottom-most surface of the water tank main part, an entirety of the flange section being disposed outside the water tank main part,
   wherein the flange section is formed of a flexible material that is capable of following the outer surface of the patient's body wall, and the flange section is configured to be brought into close contact with the outer surface of the patient's body wall to provide a liquid-tight connection between the water tank main part and the patient's body wall to prevent the leakage of liquid between the patient's body wall and the water tank main part.

2. The body-wall-contact-type water tank according to claim 1, wherein:
   the water tank is configured to be used with a retractor that has a pair of flange sections on upper and lower ends of the retractor, the pair of flange sections being configured to be fitted to the incision, and
   a circumferential edge of the bottom-most surface of the water tank main part is configured to be slidingly inserted in between the flange sections on the upper end of the retractor and the outer surface of the patient's body wall, thereby configuring the water tank main part to be connected to the incision.

3. The body-wall-contact-type water tank according to claim 1, wherein:
   the water tank is configured to be used with a retractor that has a pair of flange sections on upper and lower ends of the retractor, the pair of flange sections being configured to be fitted to the incision, and
   an inner circumferential surface of the bottom-most surface of the water tank main part has a groove that is configured to receive a rim of the flange section on the upper end of the retractor, thereby configuring the water tank main part to be connected to the incision.

4. The body-wall-contact-type water tank according to claim 1, further comprising a surgical drape that outwardly extends from the entire circumference of the flange section of the water tank main part, and that is provided with a medical adhesive on one side of the surgical drape,
   wherein the surgical drape is configured to be brought into close contact with the outer surface of the patient's body wall, to thereby connect the water tank main part to the patient's body wall.

5. The body-wall-contact-type water tank according to claim 1, wherein either a fluid feed nozzle for discharging the fluid into the water tank main part or a fixture mechanism to which the fluid feed nozzle is detachably attached is fixedly mounted on the water tank main part.

6. The body-wall-contact-type water tank according to claim 5, wherein the fluid feed nozzle or the fixture mechanism fixedly mounted on the water tank main part is arranged at a position and attitude that causes the fluid discharged from the fluid feed nozzle to flow in an obliquely downward direction along an inner surface of the water tank main part.

7. The body-wall-contact-type water tank according to claim 1, wherein the water tank main part is composed of a material that is transmissive to ultrasonic waves.

8. An in-cavity fluid perfusion system comprising:
   a body-wall-contact-type water tank according to claim 1;
   a feed means that feeds the fluid into the body-wall-contact-type water tank;
   a suction means that sucks, inside the body cavity, the fed fluid and discharges the fluid cut of the patient's body cavity, and
   a control means that controls actuation of the feed means and the suction means to perfuse the fluid.

9. The body-wall-contact-type water tank according to claim 1, wherein the water tank is self-standing while storing the liquid or can be supported by another member while storing the liquid.

\* \* \* \* \*